United States Patent
Li et al.

(10) Patent No.: US 7,400,706 B2
(45) Date of Patent: Jul. 15, 2008

(54) METHOD AND APPARATUS FOR LIQUID SAFETY-DETECTION BY BACKSCATTER WITH A RADIATION SOURCE

(75) Inventors: Yulan Li, Beijing (CN); Haifeng Hu, Beijing (CN); Yinong Liu, Beijing (CN); Zhiqiang Chen, Beijing (CN); Kejun Kang, Beijing (CN); Li Zhang, Beijing (CN); Wanlong Wu, Beijing (CN); Yuanjing Li, Beijing (CN); Yi Wang, Beijing (CN); Wenjun He, Beijing (CN); Mingrui Qi, Beijing (CN)

(73) Assignees: Tsinghua University, Beijing (CN); NucTech Company Limited, Beijing (CN)

( * ) Notice: Subject to any disclaimer, the term of this patent is extended or adjusted under 35 U.S.C. 154(b) by 75 days.

(21) Appl. No.: 11/285,395

(22) Filed: Nov. 23, 2005

(65) Prior Publication Data

US 2006/0133566 A1 Jun. 22, 2006

(30) Foreign Application Priority Data

Nov. 26, 2004 (CN) .................. 2004 1 0009895

(51) Int. Cl.
*G01N 23/203* (2006.01)
(52) U.S. Cl. .......................... 378/89; 378/86
(58) Field of Classification Search ............ 378/57, 378/70, 76, 79, 86, 87, 88, 89, 90
See application file for complete search history.

(56) References Cited

U.S. PATENT DOCUMENTS 4,475,225 A 10/1984 Galy et al.

(Continued)

FOREIGN PATENT DOCUMENTS

CN 2356344 Y 12/1999

(Continued)

OTHER PUBLICATIONS

Wang, Q., et al., "Review of X-ray Security Inspection Technology," *CT Theory and Applications* 13:32-37, China National Publications Import & Export Co. (Feb. 2004).

(Continued)

*Primary Examiner*—Allen C. Ho
(74) *Attorney, Agent, or Firm*—Sterne, Kessler, Goldstein & Fox P.L.L.C.

(57) ABSTRACT

A method and an apparatus for liquid safety-detection by backscattering with a radiation source are provided that relate to a radiation detecting technology field. The invention comprises using a radiation source, a collimator, a detector, a data collector and a computer data processor, and has the main steps of: 1) placing a liquid article to be detected onto a rotatable platform; 2) emitting a ray from the radiation source, said ray causing Compton scattering at the surface of the liquid after passing through the package layer of the liquid article; 3) the scattering photons being received by the detector after passing the collimator; 4) the detector transmitting the received data to the data collector; and 5) the data collector transmitting the amplified and shaped data to the computer data processor, which processes the data to obtain the liquid density of the detected article, then compares the result with the densities of dangerous articles in a current database, and gives a warning if the density of the detected article is consistent with that of a dangerous article. Compared to the prior art, the invention is convenient to use, detects rapidly and accurately, has a strong anti-interference, is very safe and reliable to use, and protection is easy.

10 Claims, 1 Drawing Sheet

U.S. PATENT DOCUMENTS

| | | | |
|---|---|---|---|
| 4,989,225 A * | 1/1991 | Gupta et al. | 378/10 |
| 5,181,234 A * | 1/1993 | Smith | 378/87 |
| 5,247,561 A * | 9/1993 | Kotowski | 378/87 |
| 5,428,657 A * | 6/1995 | Papanicolopoulos et al. | 378/86 |
| 5,692,029 A * | 11/1997 | Husseiny et al. | 378/88 |
| 5,729,582 A * | 3/1998 | Ham et al. | 378/89 |
| 6,104,776 A * | 8/2000 | Oikawa | 378/22 |
| 6,459,760 B1 * | 10/2002 | D'Ambrosio | 378/43 |
| 6,553,094 B1 * | 4/2003 | Bernardi et al. | 378/57 |
| 6,563,906 B2 * | 5/2003 | Hussein et al. | 378/89 |
| 6,661,867 B2 | 12/2003 | Mario et al. | |
| 6,785,360 B1 * | 8/2004 | Annis | 378/137 |
| 7,092,485 B2 * | 8/2006 | Kravis | 378/57 |
| 2004/0109532 A1 * | 6/2004 | Ford et al. | 378/57 |

FOREIGN PATENT DOCUMENTS

| | | |
|---|---|---|
| CN | 1334458 A | 2/2002 |
| WO | WO 01/94984 A2 | 12/2001 |

OTHER PUBLICATIONS

International Search Report for International Application No. PCT/CN2005/001997, mailed on Mar. 9, 2006, Intellectual Property Office, China.

* cited by examiner

METHOD AND APPARATUS FOR LIQUID SAFETY-DETECTION BY BACKSCATTER WITH A RADIATION SOURCE

CROSS REFERENCE TO RELATED APPLICATIONS

The present application claims priority to Chinese Application No. 200410009895.1 filed with the Chinese Patent Office on Nov. 26, 2004, the entirety of which is incorporated into this application by reference.

FIELD OF THE INVENTION

The invention relates to the technology field of radiation detection, and in particular, to a method and apparatus for the detection of the safety of a liquid by backscattering with a radiation source.

DESCRIPTION OF THE PRIOR ART

In the safety detection system used in civil aviation, liquid articles that passengers take with them are required to be examined without opening the articles. The detection methods used in the prior art mainly comprise a chemical method, an electromagnetic method and a neutron detection method. The chemical method is further classified into an odor identification method and an ion scanning explosive detection method and the like. The chemical detection methods often fail to accomplish detection in practical applications because the liquid articles are sealed and packaged. Further, the chemical method suffers from being very sensitive and from having a high error detection ratio. The electromagnetic detection method is prone to electromagnetic interference due to its weak signal, and cannot be used to detect liquid articles with metal packages. The use of the neutron detection method will cause residual radiation to remain in the detected liquid because of the "neutron activation." Also, radiation shielding is complicated, and has poor stability, a large cover area and a high investment, so that the method is not suitable for large scale applications in the safety detection system of civil aviation. In the existing X-ray scanning detection systems, the X-rays that are passed through a detected article are detected by a detector that reflects the density distribution in the detected article depending on the intensity variation of the X-ray. The intensity of the X-ray is converted into an image grey scale so that the perspective image of the detected article is obtained. Such an X-ray scanning detection method, which forms an image by identifying the density differences in the detected article, fails to form an image for a liquid article that has a uniform density distribution.

SUMMARY OF THE INVENTION

In order to overcome the defects existing in the prior art, the purpose of the invention is to provide for liquid safety-detection by backscattering with a radiation source. The present apparatus can be used for the safety detection of a liquid article by backscattering without needing to open the liquid article's package to obtain the density information of the detected liquid. The apparatus of the invention has the advantages of small volume, convenience in use, detection that is rapid and accurate, strong anti-interference, high safety and reliability, and protection is easy. The method and the apparatus are applicable to safety detection systems of civil aviation and other important sites.

In order to achieve the above-mentioned purposes of the invention, the technical solution of the invention is realized in the following manner.

A method for liquid safety-detection by backscattering with a radiation source is provided. The method comprises using a radiation source, a collimator, a detector, a data collector and a computer data processor. The main steps of the method are:

1) placing a liquid article that is to be detected onto a rotatable platform;

2) emitting a ray of radiation from the radiation source that causes Compton scattering at the surface of the liquid after passing through the package layer of the liquid article;

3) receiving scattered photons from the Compton scattering by the detector after passing the photons through the collimator;

4) transmitting the data that the detector has received to the data collector, by the detector; and 5) transmitting, by the data collector, the amplified and shaped data to the computer data processor, which processes the data to obtain the liquid density of the detected liquid article, and then compares the result with the densities of dangerous articles in a current database, and gives a warning if the density of the detected article is found to be consistent with that of a dangerous article.

An apparatus realizing the above described method for liquid safety-detection by backscattering with a radiation source is provided. The apparatus comprises a radiation source, a collimator, a detector, a data collector having an amplifying and shaping circuit and a computer data processor having a database of substance densities of dangerous articles. The structural features of the apparatus are that said radiation source is located on one side of a rotary platform mechanism on which a liquid article to be detected can be placed, and that said detector is located on same side as the radiation source and faces the Compton scattering beam of the detected liquid article. The collimator is placed in front of the detector. The data output wire of the detector is connected with the data collector, and the data collector is connected with the computer data processor.

In the above described apparatus, said radiation source employs an X-ray machine or an isotope.

In the above described apparatus, said detector employs a solid detector array constituted by scintillation crystal coupling photodiodes.

The invention provides an apparatus for liquid safety-detection by backscattering with a radiation source. The apparatus comprises a radiation source, a collimator, a detector, a data collector having an amplifying and shaping circuit and a computer data processor having a database of substance densities of dangerous articles, the apparatus being characterized by that said radiation source is located on one side of a rotary platform mechanism on which a liquid article to be detected can be placed, that said detector is located on same side as the radiation source and faces the Compton scattering beam of the detected liquid article, that the collimator is placed in front of the detector, that the data output wire of the detector is connected with the data collector, and that the data collector is connected with the computer data processor.

The apparatus according to the invention is characterized by that said radiation source (1) employs an X-ray machine or an isotope.

The apparatus according to the invention is characterized by that said detector (3) employs a solid detector array (7) constituted by scintillation crystal coupling photodiodes.

The invention provides a method for liquid safety-detection by backscattering with a radiation source that uses said apparatus, which method comprises using a radiation source, a collimator, a detector, a data collector and a computer data processor, and has the main steps of:

1) placing a liquid article that is to be detected onto a rotatable platform;

2) emitting a ray of radiation from the radiation source that causes Compton scattering at the surface of the liquid after passing through the package layer of the liquid article;

3) receiving scattered photons from the Compton scattering by the detector after passing the photons through the collimator;

4) transmitting the data that the detector has received to the data collector by the detector; and 5) transmitting, by the data collector, the amplified and shaped data to the computer data processor, which processes the data to obtain the liquid density of the detected liquid article, then compares the result with the densities of dangerous articles in a current database, and gives an alarm if the density of the detected article is found to be consistent with that of a dangerous article.

The invention used in above described methods uses a radiation source to detect a liquid article. The rotation of the liquid article can be controlled so as to obtain the density information of the detected liquid article. The density information of the detected liquid article is then compared with the density values of dangerous liquids that are stored in a current database. Thus, whether or not the detected liquid is a dangerous article can be judged. Compared to the prior art, the invention is convenient to use, detects rapidly and accurately, has a strong anti-interference, is very safe and reliable to use, and protection is easy.

DETAILED DESCRIPTION OF THE PREFERRED EMBODIMENT

Figure 1:
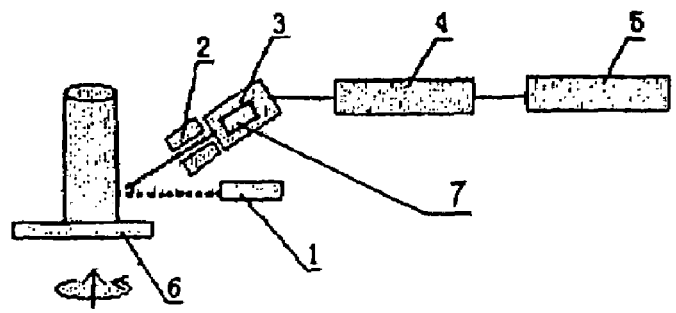
FIG. 1 is a schematic diagram of the structure of the invention.
Figure 2:
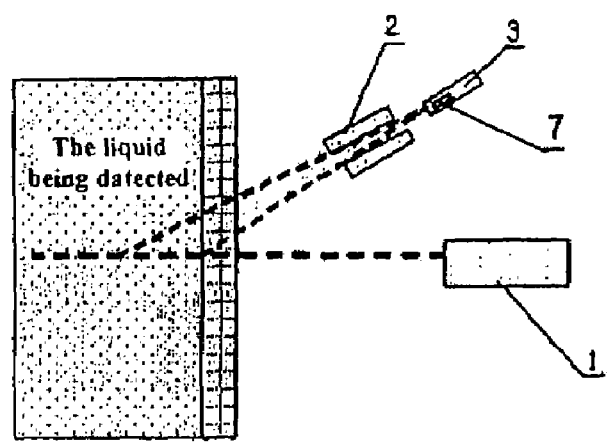
FIG. 2 is a partial enlarged diagram of the backscattering safety-detection of the invention.

Referring to FIG. 1, the invention comprises a radiation source 1 employing an X-ray machine or an isotope, a collimator 2, a detector 3 employing a solid detector array 7 constituted by scintillation crystal coupling photodiodes, a data collector 4 having an amplifying and shaping circuit and a computer data processor 5 having a database of substance densities of dangerous articles. The radiation source 1 is located on one side of a rotary platform mechanism 6 on which a liquid article to be detected can be placed, and the detector 3 is located on the same side as the radiation source 1 and faces the Compton scattering beam of the detected liquid article. The collimator 2 is placed in front of the detector 3. The data output wire of the detector 3 is connected with the data collector 4, and the data collector 4 is connected with the computer data processor 5.

The steps in the application of the apparatus of the invention are:

1) A liquid article to be detected is placed onto the rotary platform mechanism 6.

2) The radiation source 1 emits a ray of radiation that causes Compton scattering at the surface of the liquid after passing through the package layer of the liquid article;

3) The scattered photons from the Compton scattering are received by the detector 3 after passing the collimator 2;

4) The detector 3 transmits the received data to the data collector 4;

5) The data collector 4 transmits the amplified and shaped data to the computer data processor 5, which processes the data to obtain the liquid density of the detected article, then compares the result with the densities of dangerous articles in a current database, and gives a warning if the density of the detected article is found to be consistent with that of a dangerous article.

We claim:

1. A method for detecting the safety of a liquid in a packaged liquid article by backscattering with a radiation source, said method comprising:

1) placing said packaged liquid article onto a rotatable platform;

2) emitting a beam of radiation from a radiation source, said beam of radiation causing Compton scattering at the surface of said liquid in said liquid article after passing through said liquid article's package;

3) receiving scattered photons from said Compton scattering by a detector after passing said photons through a collimator;

4) transmitting said detector's data that is to be output to a data collector, by said detector; and 5) transmitting, by said data collector, data that has been amplified and shaped by said data collector to a computer data processor, and 6) processing said amplified and shaped data to obtain a density for said liquid, then 7) comparing said density of said liquid with the densities of dangerous articles in a database, and 8) giving a warning if the density of said liquid in said liquid article is found to be consistent with that of a dangerous article in said database, by said processor.

2. The method according to claim 1, wherein said radiation source employs an X-ray machine or an isotope as the source of said radiation.

3. The method according to claim 1 or claim 2, wherein said detector employs a solid detector array having scintillation crystal coupling photodiodes.

4. An apparatus for detecting the safety of a liquid in a packaged liquid article by backscattering with a radiation source, said apparatus comprising a radiation source (1) for emitting a ray of radiation that causes Compton scattering at the liquid surface of said liquid article after passing through said liquid article's package, a collimator (2), a detector (3), a data collector (4) having an amplifying and shaping circuit and a computer data processor (5) having a database of substance densities of dangerous liquids, said apparatus being characterized by that said apparatus further comprises a rotary platform (6) on which said packaged liquid article is placed and that said radiation source (1) is located on one side of the rotary platform (6), that said detector (3) is located on the same side as the radiation source (1) and faces a Compton scattering beam from the detected liquid article, that the collimator (2) is placed in front of the detector (3), that a data output of the detector (3) is connected to the data collector (4), and that the data collector (4) is connected to the computer data processor (5).

5. The apparatus according to claim 4, characterized by that said radiation source (1) employs an X-ray machine or an isotope as the source of said radiation.

6. The apparatus according to claim 4 or 5, characterized by that said detector (3) employs a solid detector array (7) having scintillation crystal coupling photodiodes.

7. A method for detecting the safety of a liquid in a packaged liquid article by backscattering with a radiation source, said method comprising 1) placing said article in an apparatus that comprises: a radiation source (1), that emits a beam of radiation that causes Compton scattering at a surface layer of liquid after passing through a package layer of a liquid article, a collimator (2), a detector (3), a data collector (4) having an amplifying and shaping circuit and a computer data processor (5) having a database of substance densities of known dangerous liquids, characterized by that said apparatus further comprises a rotary platform (6) on which said packaged liquid article to be detected can be placed and that said radiation source (1) is located on one side of said rotary platform (6), that said detector (3) is located on same side as the radiation source (1) and faces a Compton scattering beam of said packaged liquid article, that the collimator (2) is placed in front of the detector (3), that said detector's (3) data output is connected to the data collector (4), and that the data collector (4) is connected to the computer data processor (5)

2) emitting a beam of radiation from said radiation source, said beam of radiation causing Compton scattering at the surface of said liquid in said liquid article after passing through said liquid article's package;

3) receiving scattered photons from said Compton scattering by a detector after passing said photons through said collimator;

4) transmitting said detector's data that is to be output to said data collector, by said detector; and 5) transmitting, by said data collector, data that has been amplified and shaped by said data collector to said computer data processor, 6) processing said amplified and shaped data to obtain a density for said liquid, then 7) comparing said density of said liquid with the densities of said known dangerous liquids in said database, and 8) giving a warning by said processor if the density of said liquid in said liquid article is found to be consistent with that of a known dangerous liquid in said database.

8. The method according to claim 7, characterized by that said radiation source (1) employs an X-ray machine or an isotope as the source of said radiation.

9. The method according to claim 7 or claim 8, characterized by that said detector (3) employs a solid detector array (7) having scintillation crystal coupling photodiodes.

10. The method according to any one of claim 1 or claim 7, wherein said packaged liquid article on said platform is rotated.

* * * * *